(12) United States Patent
Yang et al.

(10) Patent No.: US 9,395,304 B2
(45) Date of Patent: Jul. 19, 2016

(54) NANOSCALE STRUCTURES ON OPTICAL FIBER FOR SURFACE ENHANCED RAMAN SCATTERING AND METHODS RELATED THERETO

(71) Applicant: LAWRENCE LIVERMORE NATIONAL SECURITY, LLC, Livermore, CA (US)

(72) Inventors: Xuan Yang, San Jose, CA (US); Tiziana C. Bond, Livermore, CA (US); Jerald Britten, Clayton, CA (US); Thomas C. Carlson, Livermore, CA (US); Nazar Ileri, Livermore, CA (US); Cindy Larson, Tracy, CA (US); Claire Gu, Santa Cruz, CA (US)

(73) Assignees: Lawrence Livermore National Security, LLC, Livermore, CA (US); The Regents of The University of California, Oakland, CA (US)

( * ) Notice: Subject to any disclaimer, the term of this patent is extended or adjusted under 35 U.S.C. 154(b) by 423 days.

(21) Appl. No.: 13/901,448

(22) Filed: May 23, 2013

(65) Prior Publication Data

US 2015/0369744 A1 Dec. 24, 2015

Related U.S. Application Data

(60) Provisional application No. 61/691,036, filed on Aug. 20, 2012.

(51) Int. Cl.
*G01N 21/65* (2006.01)
*C23C 14/34* (2006.01)
(Continued)

(52) U.S. Cl.
CPC .............. *G01N 21/658* (2013.01); *B82Y 40/00* (2013.01); *C23C 14/34* (2013.01); *G02B 6/0229* (2013.01); *G02B 6/02052* (2013.01); *G01N 2201/06113* (2013.01); *G01N 2201/088* (2013.01)

(58) Field of Classification Search
CPC ................ G01N 21/65; G01N 21/658; G01N 2021/656; G01N 2201/088; G01J 3/02; G01J 3/44

See application file for complete search history.

(56) References Cited

U.S. PATENT DOCUMENTS 3,751,992 A 8/1973 Morgan
5,311,426 A 5/1994 Donohue et al.
(Continued)

FOREIGN PATENT DOCUMENTS

FR 2679689 1/1993
FR 2782228 2/2000
(Continued)

OTHER PUBLICATIONS

Chang et al. "Nanopillars array for surface enhanced Raman scattering," Proc. SPIE8024, 80240I, 80240I-8 (2011).*
(Continued)

*Primary Examiner* — Michael A Lyons
*Assistant Examiner* — Dominic J Bologna
(74) *Attorney, Agent, or Firm* — Steinfl & Bruno, LLP

(57) ABSTRACT

A nanoscale structure fabricated on a planar end facet of an optic fiber is described, to enable detection of molecules by surface-enhanced Raman scattering. The nanoscale structure may comprise an array of nanopillars. The nanoscale structure may also comprise a non periodic, or random, surface-relief structure. The nanoscale structure may be coated in a metal, comprising, for example, silver, gold, aluminum, iridium, platinum, palladium, copper, or a combination of the same. The nanoscale structure may be fabricated on a planar end facet of an optical fiber by interference lithography.

14 Claims, 11 Drawing Sheets

(51) Int. Cl.
*B82Y 40/00* (2011.01)
*G02B 6/02* (2006.01)

(56) References Cited

U.S. PATENT DOCUMENTS

| | | | |
|---|---|---|---|
| 5,401,897 A | 3/1995 | Depalle et al. | |
| 5,485,277 A | 1/1996 | Foster | |
| 5,496,701 A | 3/1996 | Pollard-Knight | |
| 5,500,900 A | 3/1996 | Chen et al. | |
| 5,596,644 A | 1/1997 | Abel et al. | |
| 5,832,165 A | 11/1998 | Reichert et al. | |
| 5,843,767 A | 12/1998 | Beattie | |
| 5,866,430 A | 2/1999 | Grow | |
| 6,023,540 A | 2/2000 | Walt et al. | |
| 6,146,767 A | 11/2000 | Schwartz | |
| 6,356,676 B1 | 3/2002 | Herron et al. | |
| 6,468,823 B1 | 10/2002 | Scherer et al. | |
| 6,611,634 B2 | 8/2003 | Herron et al. | |
| 6,643,439 B2 | 11/2003 | Notomi et al. | |
| 6,710,879 B1 | 3/2004 | Hansen et al. | |
| 6,738,551 B2 | 5/2004 | Noda et al. | |
| 6,785,432 B2 | 8/2004 | Letant et al. | |
| 6,801,677 B1 | 10/2004 | Grace et al. | |
| 6,829,073 B1 | 12/2004 | Krol et al. | |
| 6,867,900 B2 | 3/2005 | Weisbuch et al. | |
| 7,026,640 B2 | 4/2006 | Nathan et al. | |
| 7,027,676 B2 | 4/2006 | VanWiggeren et al. | |
| 7,155,076 B2 | 12/2006 | Letant et al. | |
| 7,206,488 B1 | 4/2007 | Altug et al. | |
| 7,289,221 B2 | 10/2007 | Wang et al. | |
| 7,318,907 B2 | 1/2008 | Stark et al. | |
| 7,351,588 B2 | 4/2008 | Poponin | |
| 7,388,661 B2 | 6/2008 | Li et al. | |
| 7,476,787 B2 | 1/2009 | Thomas et al. | |
| 7,492,979 B2 | 2/2009 | Wang et al. | |
| 7,713,849 B2 | 5/2010 | Habib et al. | |
| 8,059,824 B2 | 11/2011 | Pallone et al. | |
| 8,059,924 B1 | 11/2011 | Letant et al. | |
| 8,187,481 B1* | 5/2012 | Hobbs | 216/24 |
| 8,427,639 B2 | 4/2013 | Moskovits et al. | |
| 8,780,439 B2 | 7/2014 | Bora et al. | |
| 8,830,450 B2 | 9/2014 | Bond et al. | |
| 8,947,657 B2 | 2/2015 | Letant et al. | |
| 9,080,981 B2 | 7/2015 | Bond et al. | |
| 2003/0128956 A1* | 7/2003 | Sharma et al. | 385/145 |
| 2003/0133639 A1 | 7/2003 | Tao et al. | |
| 2003/0143580 A1 | 7/2003 | Straus | |
| 2004/0021193 A1 | 2/2004 | Nathan et al. | |
| 2004/0023396 A1 | 2/2004 | Boyd et al. | |
| 2004/0067163 A1 | 4/2004 | Prasad et al. | |
| 2005/0078903 A1 | 4/2005 | Grace et al. | |
| 2005/0084980 A1 | 4/2005 | Koo et al. | |
| 2005/0135723 A1 | 6/2005 | Carr et al. | |
| 2005/0206895 A1 | 9/2005 | Salmelainen | |
| 2006/0072642 A1 | 4/2006 | Wang et al. | |
| 2006/0085200 A1 | 4/2006 | Allamanche et al. | |
| 2007/0160216 A1 | 7/2007 | Nicol et al. | |
| 2008/0008323 A1 | 1/2008 | Hilpert et al. | |
| 2008/0080816 A1* | 4/2008 | D'Urso et al. | 385/77 |
| 2008/0094621 A1* | 4/2008 | Li et al. | 356/301 |
| 2008/0174775 A1 | 7/2008 | Moskovits | |
| 2009/0244532 A1 | 10/2009 | Letant et al. | |
| 2010/0177903 A1 | 7/2010 | Vinton et al. | |
| 2011/0075848 A1 | 3/2011 | Purnhagen et al. | |
| 2011/0128536 A1 | 6/2011 | Bond et al. | |
| 2011/0166045 A1 | 7/2011 | Dhawan et al. | |
| 2012/0081703 A1 | 4/2012 | Moskovits et al. | |

FOREIGN PATENT DOCUMENTS

| | | |
|---|---|---|
| FR | 2851879 | 9/2004 |
| WO | 01/36945 | 5/2001 |
| WO | 2005/069272 | 7/2005 |
| WO | 2007/104877 | 9/2007 |
| WO | WO2012/015443 * | 2/2012 |

OTHER PUBLICATIONS

R. Jarvis et al. "Discrimination of Bacteria Using Surface-Enhanced Raman Spectroscopy" Analytical Chemistry, vol. 76, No. 1, Jan. 1, 2004. p. 40-47.

T. Vo-Dinh et al. "Cancer gene detection using surface-enhanced Raman scattering (SERS)" Journal of Raman Spectroscopy vol. 33, Issue 7, Jul. 2002. p. 511-516 Abstract Only.

X. Yang et al. "Nanopillar array on a fiber facet for sensitive surface-enhanced Raman scattering" Optics Express, vol. 20 No. 22, Oct. 22, 2012. p. 24819-24826.

E. Chow et al "Ultracompact biochemical sensor built with two-dimensional photonic crystal microcavity" Optics Letters vol. 29, Issue 10, 2004. p. 1093-1095.

L. Chan et al. "Self-referenced assay method for photonic crystal biosensors: Application to small molecule analytes" Sensors and Actuators B Chemical, vol. 120, No. 2, Jan. 2007. p. 392-398.

V. Lin et al. "A Porous Silicon-Based Optical Interferometric Biosensor" Science vol. 278, No. 5339. Oct. 31, 1997 p. 840-843.

F. Morhard et al "Immobilization of antibodies in micropatterns for cell detection by optical diffraction" Sensors and Actuators B 70 (2000) p. 232-242.

M. Loncar et al. "Photonic crystal laser sources for chemical detection" Applied Physics Letters vol. 82, No. 26. Jun. 30, 2003 p. 4648-4650.

B. Schmidt et al "Nanocavity in a silicon waveguide for ultrasensitive nanoparticle detection" Applied Physics Letters vol. 85, No. 21. Nov. 22, 2004 p. 4854-4856.

M.J. Levene et al "Zero-Mode Waveguides for Single-Molecule Analysis at High Concentrations" Science vol. 299, Jan. 31, 2003. p. 682-686.

M. Lee et al. "Nanoscale microcavity sensor for single particle detection" Optics Letters 2007, 32: 3284-3286.

S. Chan et al. "Identification of Gram Negative Bacteria Using Nanoscale Silicon Microcavities" Journal of the American Chemical Society. 2001, 123, pp. 11797-11798.

S. Letant et al. "Functionalized silicon membranes for selective bio-organism capture". Nature Materials, vol. 2, Jun. 2003 p. 391-395.

S. Letant et al. Enzyme immobilization on porous silicon survaces:, Advanced Materials vol. 16, No. 8, Apr. 19, 2004 p. 689-693.

B. Hart et al "New method for attachment fo biomolecules to porous silicon" Chem. Commun. 2003 p. 322-323.

Baker, S. et al., Detection of Bio-organism stimulants using random binding on a defect-free photonic crystal, Applied Physics Letters 2010 (in press).

Letant, S., et al., Integration of porous silicon chips in an electronic artificial nose, Sensors and Actuators B 2000, 69: 193-198.

Nilsson, J., et al., Localized functionalization of single nanopores, Advanced Materials 2006, 18: 427-431.

Katz, A., In situ determination of refractive index and size of *Bacillus* spores by light transmission, Optics Letters 2005, 30: 589-591.

Grow, A., et al., New biochip technology for label-free detection of pathogens and their toxins, Journal of Microbiological Methods 2003, 221-233.

Nguyen, B., et al., Membrane-Based Electrochemical Nanobiosensor for the Detection of Virus, Anal. Chem. 2009, 81: 7226-7234.

Dorfner, D., et al., Silicon photonic crystal nanostructures for refractive Index sensing, Applied Physics Letters 2008, 93: 181103-1-181103-3.

Larsson, E., et al., Sensing Characteristics of NIR Localized Surface Plasmon Resonances in Gold Nanorings for Application as Ultrasensitive Biosensors, Nano Letters 2007, 7: 1256-1263.

Vollmer, F., et al., Single virus detection from the reactive shift of a whispering-gallery mode, PNAS 2008, 105: 20701-20704.

Hagino, H., et al., Effects of fluctuation in air hole radii and positions on optical characteristics in photonic crystal heterostructure nanocavities, Physical Review B 2009, 79: 085112-1-085112-8.

Rea, I., et al., Fabrication and characterization of a porous silicon based microarray for label-free optical monitoring of biomolecular interactions, Journal of Applied Physics 2010, 107: 014513-1-014513-4.

(56) References Cited

OTHER PUBLICATIONS

Guicheteau, J., et al., Bacillus Spore Classification via Surface-Enhanced Raman Spectroscopy and Principal Component Analysis, Applied Spectroscopy 2008, 62: 267-272.
Lee, J., Real-time detection of airborne viruses on a mass-sensitive device, Applied Physics Letters 2008, 93: 013901-1-013901-3.
Fitch, J., et al., Technology Challenges in Responding to Biological or Chemical Attacks in the Civilian Sector, Science 2003, 302: 1350-1354.
Hodges, L., et al., National validation study of a swab protocol for the recovery of Bacillus anthracis spores from surfaces, Journal of Microbiological Methods 2010, 141-146.
Cyrklaff, M., et al., Cryo-electron tomography of vaccinia virus, PNAS 2005, 102: 2272-2777.
Schwartz, M., et al., The Smart Petri Dish: A Nanostructured Photonic Crystal for Real-Time Monitoring of Living Cells, Langmuir 2006, 22: 7084-7090.
Buttner, M., et al., Determination of the Efficacy of Two Building Decontamination Strategies by Surface Sampling with Culture and Quantitative PCR Analysis, Applied and Environmental Microbiology 2004, 70: 4740-4747.
Lee, M., et al., Nanoscale microcavity sensor for single particle detection, Optics Letters 2007, 32: 3284-3286.
Mortensen, N., et al., Liquid-infiltrated photonic crystals enhanced light-matter interactions for lab-on-a-chip applications, Microfluid Nanofluid 2008, 4: 117-127.
Skottrup, P., et al., Towards on-site pathogen detection using antibody-based sensors, Biosensors and Bioelectronics 2008, 24: 339-348.
Golightly, R., et al., Surface-Enhanced Raman Spectroscopy and Homeland Security: A Perfect Match?, AC Nano 2009, 3: 2859-2869.
Van Der Heijden, R., et al., InP-based two-dimensional photonic crystals filled with polymers, Applied Physics Letters 2006, 88: 161112-1-161112-3.
Buswell, SC, et al., Specific detection of proteins using photonic crystal waveguides, Optics Express 2008, 16: 15949-15957.
Lee, S., et al., Improved Localized Surface Plasmon Resonance Immunoassay with Gold Bipyramid Substrates, Anal. Chem. 2009, 81: 4450-4455.
Letant, SE, et al., Most-Probable-Number Rapid Viability PCR method to detect viable spores of Bacillus anthracis in swab samples, Journal of Microbiological Methods 2010, 81: 200-202.
Kane, SR, et al., Rapid, high-throughput, culture-based PCR methods to analyze samples for viable spores of Bacillus anthracis and its surrogates, Journal of Microbiological Methods 2009, 278-284.
Lin, S., et al., Design of nanoslotted photonic crystal waveguide cavities for single nanoparticle trapping and detection, Optics Letters 2009, 34: 3451-3453.
Alexander, T., et al., Characterization of a commercialized SERS-active substrate and its application to the identification of intact Bacillus endospores, Applied Optics 2007, 46: 3878-3890.
Asano, T., et al., Analysis of the experimental Q factors (~1 million) of photonic crystal nanocavities, Optics Express 2006, 14: 1996-2002.
Non-Final Office Action mailed by the USPTO on Mar. 31, 2011 for U.S. Appl. No. 12/206,337, filed Sep. 8, 2008.
Notice of Allowance mailed by the USPTO on Jul. 14, 2011 for U.S. Appl. No. 12/206,337, filed Sep. 8, 2008 in the name of Lawrence Livermore.
Aizpurua, J., et al., Optical properties of gold nanorings, Physical Review Letters 2003, 90: 057401-1-057401-4.
Bora, M., et al., Plasmon resonant cavities in vertical nanowire arrays, Nano Letters 2010, 10: 2832-2837.
Etchegoin, P. G., et al., A perspective on single molecule SERS: Current status and future challenges, Physical Chemistry Chemical Physics 2008, 10: 6079-6089.
Gartia, M., et al., Rigorous surface enhanced Raman spectral characterization of large-area high-uniformity silver-coated tapered silica nanopillar arrays, Nanotechnology 2010, 21: 395701-1-395701-9.

Goddard, L., et al., Rapidly reconfigurable all-optical universal logic gates, Proc. of SPIE 2006, 6368: 63680H-1-63680H-13.
Johansson, A., et al., Sampled-grating DBR laser-based analog optical transmitters, Journal of Lightwave Technology 2003, 21: 2968-2976.
Murray, C. A., et al., Silver-molecule separation dependence of surface-enhanced Raman scattering, Physical Review Letters 1981, 46: 57-60.
Nakatsuhara, K., et al., All-optical set-reset operation in a distributed feedback GaInAsP waveguide, IEEE Photonics Technology Letters 1998, 10: 78-80.
Netti, C., et al., Reliable substrate technology for surface enhanced Raman spectroscopy, Raman Technology for Today's Spectroscopists 2005, 3-8.
Pan, G., et al., Optical injection induced polarization bistability in vertical cavity surface emitting lasers, Appl. Phys. Lett. 1993, 63: 2999-3001.
Pocha, M. et al., Gain Lever Characterization in Monolithically Integrated Diode Lasers, Physics & Simulation of Optoelec. Devices 2005, 5772: 288-298.
Tanenaka, M., et al., Realization of All-Optical Flip-Flop Using Directionally Coupled Bistable Laser Diode, IEEE Photo. Tech. Let. 2004, 16: 45-47.
Tanenaka, M., et al., Multimode Interference Bistable Laser Diode, IEEE Photo. Tech. Let. 2003, 15: 1035-1037.
Uenohara, H., et al., Operation characteristics of a side-light-injection multiple quantum well bistable laser for all-optical switching, Jpn. J. Appl. Phys. 1994, 815-821.
Wen, P., et al., Observation of bistability in a Vertical-Cavity Semiconductor Optical Amplifier (VCSOA), Optical Society of America 2002, 10: 1273-1278.
Zhou, J., et al., All-optical bistable switching dynamics in 1.55 μm two-segment strained multiquantum-well distributed-feedback lasers, Journal of Lightwave Technology 1997, 15: 342-355.
Fernandez, A., et al., Use of interference lithography to pattern arrays of submicron resist structures for field emission flat panel displays, J. Vac. Sci. Technol. B 1997, 15: 729-735.
Welty, R. J., et al., Integrated laser with low-loss high index-contrast waveguides for OEICs, SPIE, International Symposium on Integrated Optoelectronic Devices, 2004, San Jose 1-14.
Non-Final Office Action mailed on May 8, 2013 for U.S. Appl. No. 12/957,883, filed Dec. 1, 2010 in the name of Tiziana C. Bond et al.
Final Office Action mailed on Nov. 13, 2013 for U.S. Appl. No. 12/957,883, filed Dec. 1, 2010 in the name of Tiziana C. Bond et al.
Non-Final Office Action mailed on Nov. 27, 2013 for U.S. Appl. No. 13/117,079, filed May 26, 2011 in the name of Sonia Edith Letant et al.
Andrade, G., et al., Multilayer silver nanoparticles-modified optical fiber tip for high performance SERS remote sensing, Biosensors & Bioelect. 2010, 25: 2770-2275.
Averitt, RD, et al., Plasmon Resonance Shifts of Au-Coated Au2S Nanoshells: Insight into Multicomponent Nanoparticle Growth, Phys. Rev. Let. 1997, 78: 4217-4220.
Chang, A., et al., Nanopillars array for surface enhanced Raman scattering, Adv. Environ. Chem. & Biol. Sensing Tech. 2010, 8024: 1-8.
Campion, A., et al., Surface-enhanced Raman scattering, Chem. Soc. Rev. 1998, 27: 241-250.
Carron, K., et al., Molecular-Specific Chromatographic Detector Using Modified SERS Substrates, Anal. Chem. 1995, 67: 3353-3356.
Dahlin, A., et al., Localized Surface Plasmon Resonance Sensing of Lipid-Membrane-Mediated Biorecognition Events, JACS 2005, 127: 5043-5048.
Dhawan, A, et al., Fabrication of nanodot plasmonic waveguide structures using FIB milling and electron beam-induced deposition, Scanning 2009, 31: 139-146.
Dmitriev, A., et al., Gold-Silica-Gold Nanosandwiches: Tunable Bimodal Plasmonic Resonators, Small 2007, 3: 294-299.
Draine, B., "The discrete-dipole approximation and its application to interstellar graphite grains", The Astrophys. Journal 1988, 333: 848-872.

(56) References Cited

OTHER PUBLICATIONS

Elghanian R., et al., "Selective Colorimetric Detection of Polynucleotides Based on the Distance-Dependent Optical Properties of Gold Nanoparticles", Science 1997, 277: 1078-1081.
El-Sayed, I., et al., "Surface Plasmon Resonance Scattering and Absorption of anti-EGFR Antibody Conjugated Gold Nanoparticles in Cancer Diagnostics: Applications in\Oral Cancer", Nano Letters 2005, 5: 829-834.
Feng, S., et al., Fiber coupled waveguide grating structures, Appl. Phys. Lett. 2010, 96: 133101-1-133101-3.
Fleischmann, M. et al., Raman spectra of pyridine assorbed at a silver electrode, Chem. Phys. Lett. 1974, 26: 163 166.
Gu, C., et al., Fiber Sensors for Molecular Detection, Info Optics & Optical Data Storage 2010, 7851: 785105-785105-14.
Guieu, V., et al., Remote surface enhanced Raman spectroscopy imaging via a nanostructured optical fiber Bundle, Optical Society of America 2009, 17: 24030-24035.
Gunnarsson, L., et al., Confined Plasmons in Nanofabricated Single Silver Particle Pairs: Experimental Observations of Strong Interparticle Interactions, J. Phys. Chem. B 2005, 109: 1079-1087.
Gutes, A., et al., Silver Nanostructures on Silicon Based on Galvanic Displacement Process, J. Phys. Chem. C 2009, 113: 16939-16944.
Haes, A., et al., A Nanoscale Optical Biosensor: Sensitivity and Selectivity of an Approach Based on the Localized Surface Plasmon Resonance Spectroscopy of Triangular Silver Nanoparticles, JACS 2002, 124: 10596-10604.
Haes, A., et al., A Localized Surface Plasmon Resonance Biosensor: First Steps toward an Assay for Alzheimer's Disease, Nano Letters 2004, 4: 1029-1034.
Hanarp, P., et al., Optical Properties of Short Range Ordered Arrays of Nanometer Gold Disks Prepared by Colloidal Lithography, J. Phys. Chem. B 2003, 107: 5768-5772.
Hanarp, P., et al., Nanostructured model biomaterial surfaces prepared by colloidal lithography, Nanostructured Materials 1999, 12: 429-432.
Hutter, E., et al., Exploitation of localized surface plasmon resonance, Adv. Mat. 2004, 16: 1685-1706.
Jansen, T., et al., Nanosphere Lithography: Effect of the External Dielectric Medium on the Surface Plasmon Resonance Spectrum of a Periodic Array of Silver Nanoparticles, J. Phys. Chem. B 1999, 103: 9846-9853.
Jansen, T., et al., Nanosphere Lithography: Surface Plasmon Resonance Spectrum of a Periodic Array of Silver Nanoparticles by Ultraviolet-Visible Extinction Spectroscopy and Electrodynamic Modeling, J. Phys. Chem. B 1999, 103: 2394-2401.
Jung, L., et al., Quantitative Interpretation of the Response of Surface Plasmon Resonance Sensors to Adsorbed Films, Langmuir 1998, 14: 5636-5648.
Kim, S., et al., Patterned Arrays of Au Rings for Localized Surface Plasmon Resonance, Langmuir 2006, 22: 7109-7112.
Kim, A., et al., Study of Molecular Trapping Inside Gold Nanofinger Arrays on Surface-Enhanced Raman Substrates, JACS 2011, 133: 8234-8239.
Kniepp, K., et al., Single Molecule Detection Using Surface-Enhanced Raman Scattering (SERS), Phys. Rev. Lett. 1997, 78: 1667-1670.
Kniepp, K., et al., Surface-enhanced Raman scattering and biophysics, J. Phys.: Condensed Matter 2002, 14: R597-R624.
Kostovski, G., et al., Nanoimprinted optical fibres: Biotemplated nanostructures for SERS sensing, Biosesnors & Bioelectronics 2009, 24: 1531-1535.
Langhammer, C., et al., Plasmonic Properties of Supported Pt and Pd Nanostructures, Nano Letters 2006, 6: 833-838.
Lucotti, A., et al., Fiber-optic SERS sensor with optimized geometry, Sensors & Actuators 2007, 121: 356-364.
Malinsky, M., et al., Chain Length Dependence and Sensing Capabilities of the Localized Surface Plasmon Resonance of Silver Nanoparticles Chemically Modified with Alkanethiol Self-Assembled Monolayers, J. Am. Chem. Soc. 2001, 123: 1471-1482.

McFarland, A., et al., Single Silver Nanoparticles as Real-Time Optical Sensors with Zeptomole Sensitivity, Nano Letters 2003, 3: 1057-1062.
Miller, M., et al., Sensitivity of Metal Nanoparticle Surface Plasmon Resonance to the Dielectric Environment, J. Phys. Chem. B 2005, 109: 21556-21565.
Mock, J., et al., Local Refractive Index Dependence of Plasmon Resonance Spectra from Individual Nanoparticles, Nano Letters 2003, 3: 485-491.
Morokoshi, S., et al., Sensing Capabilities of Colloidal Gold Modified with a Self-Assembled Monolayer of a Glucose-Carrying Polymer Chain on a Glass Substrate, Langmuir 2004, 20: 8897-8902.
Mullen, K., et al., Surface-Enhanced Raman Spectroscopy with Abrasively Modified Fiber Optic Probes, Am. Chem. Soc. 1991, 63: 2196-2199.
Nath, N., et al., A Colorimetric Gold Nanoparticle Sensor to Interrogate Biomolecular Interactions in Real Time on a Surface, Anal. Chem. 2002, 74: 504-509.
Nehl, C., et al., Optical Properties of Star-Shaped Gold Nanoparticles, Nano Letters 2006, 6: 683-688.
Nie, S., et al., Probing Single Molecules and Single Nanoparticles by Surface-Enhanced Raman Scattering, Science 1997, 275: 1102-1106.
Okamoto, T., et al., Local plasmon sensor with gold colloid monolayers deposited upon glass substrates, Optics Letters 2000, 25: 372-374.
Olofsson, L., et al., Surface-Based Gold-Nanoparticle Sensor for Specific and Quantitative DNA Hybridization Detection, Langmuir 2003, 19: 10414-10419.
Ozbay, E., Plasmonics: Merging Photonics and Electronics at Nanoscale Dimensions, Science 2006, 311: 189-193.
Prikulis, J., et al., Optical Spectroscopy of Nanometric Holes in Thin Gold Films, Nano Letters 2004, 4: 1003-1007.
Purcell, E., et al., Scattering and absorption of light by non-spherical dielectric grains, The Astrophysical Journal 1973, 186: 705-714.
Raschke, G., et al., Biomolecular Recognition Based on Single Gold Nanoparticle Light Scattering, Nano Letters 2003, 3: 935-938.
Reinhard, B., et al., Calibration of Dynamic Molecular Rulers Based on Plasmon Coupling between Gold Nanoparticles, Nano Letters 2005, 5: 2246-2252.
Rindzevicius, T., et al., Plasmonic Sensing Characteristics of Single Nanometric Holes, Nano Letters 2005, 5: 2335-2339.
Schelm, S., et al., Internal Electric Field Densities of Metal Nanoshells, J. Phys. Chem. B 2005, 109: 1689-1694.
Shanmukh, S., et al., Rapid and Sensitive Detection of Respiratory Virus Molecular Signatures Using a Silver Nanorod Array SERS Substrate, Nano Letters 2006, 6: 2630-2636.
Sherry, L., et al., Localized Surface Plasmon Resonance Spectroscopy of Single Silver Triangular Nanoprisms, Nano Letters 2006, 6: 2060-2065.
Shi, J., et al., Optical characterization of electronic transitions arising from the Au/S interface of self-assembled n-alkanethiolate monolayers, Chem. Phys. Left. 1995, 246: 90-94.
Shumaker-Parry, J., et al., Fabrication of crescent-shaped optical antennas, Adv. Mat. 2005, 17: 2131-2134.
Sönnichsen, C. et al., Spectroscopy of single metallic nanoparticles using total internal reflection microscopy, Appl. Phys. Lett. 2000, 77: 2949-2951.
Sun, Y., et al., Increased Sensitivity of Surface Plasmon Resonance of Gold Nanoshells Compared to That of Gold Solid Colloids in Response to Environmental Changes, Anal. Chem. 2002, 74: 5297-5305.
Svedhem, S., et al., Patterns of DNA-Labeled and scFv-Antibody-Carrying Lipid Vesicles Directed by Material-Specific Immobilization of DNA and Supported Lipid Bilayer Formation on an Au/SiO2 Template, ChemBioChem 2003, 4: 339-343.
Symthe, E., et al., Optical Antenna Arrays on a Fiber Facet for in Situ Surface-Enhanced Raman Scattering Detection, Nano Letters 2009, 9: 1132-1138.
Tam, F., et al., Geometrical Parameters Controlling Sensitivity of Nanoshell Plasmon Resonances to Changes in Dielectric Environment, J. Phys. Chem. B 2004, 108: 17290-17294.

(56) References Cited

OTHER PUBLICATIONS

Tao, A., et al., Langmuir-Blodgett Silver Nanowire Monolayers for Molecular Sensing Using Surface-Enhanced Raman Spectroscopy, Nano Letters 2003, 3: 1229-1233.
Viets, C., et al., Single-fibre surface-enhanced Raman sensors with angled tips, J. Raman Spectroscopy 2000, 31: 625-631.
Viets, C., et al., Comparison of fibre-optic SERS sensors with differently prepared tips, Sensors & Actuators B 1998, 51: 92-99.
Wang, H., et al., Nanorice: A hybrid plasmonic nanostructure, Nano Letters 2006, 6: 827-832.
Yang, X., et al., Highly Sensitive Detection of Proteins and Bacteria in Aqueous Solution Using Surface-Enhanced Raman Scattering and Optical Fibers, Anal. Chem. 2011, 83: 5888-5894.
Yang, X., et al., High-sensitivity molecular sensing using hollow-core photonic crystal fiber and surface-enhanced Raman scattering, J. Opt. Soc. Am. A 2010, 27: 977-1004.
Yang, X., et al., Portable fiber sensors based on surface-enhanced Raman scattering, Rev. Sci. Instruments 2010, 81: 123103-1-123103-5.
Yonzon, C., et al., A Comparative Analysis of Localized and Propagating Surface Plasmon Resonance Sensors: The Binding of Concanavalin A to a Monosaccharide Functionalized Self-Assembled Monolayer, JACS 2004, 126: 12669-12676.
Zhu, Y., et al., Development of silver nanorod array based fiber optic probes for SERS detection, Sensors & Actuators B 2011, 157: 42-50.
Webb KJ, et al., "Waveguide cavity surface enhanced Raman scattering" *Phys. Rev.* B73, 073404, 2006, Total of 4 pages.
R. Maboudian, "Letter to the editor, template assisted deposition of Ag nanoparticles arrays for surface-enhanced Raman Scattering applications" *Sensors and Actuators B* 125, 353-356, 2007.
Nilsson et al., "Fouling study of silicon oxide pores exposed to tap water" *Materials Letters* 61, 2247-2250, 2007.
Magagnin, et al. "Gold Deposition by Galvanic Displacement on Semiconductor Surfaces: Effect of Substrate on Adhesion" *J. Phys. Chem. B* 106:401-407. (2002).
Goddard et al. "Electrical and Optical Gain Lever Effects in InGaAs Double Quantum Well Diode Lasers" *Jour. Quant. Electr.* 2007, 12 pages.
Restriction Requirement mailed on Dec. 5, 2012 for U.S. Appl. No. 12/958,302, filed Dec. 1, 2010 in the name of Tiziana C. Bond.
Non-Final Office Action mailed on Jan. 16, 2013 for U.S. Appl. No. 12/958,302, filed Dec. 1, 2010 in the name of Tiziana C. Bond.
Final Office Action mailed on Aug. 6, 2013 for U.S. Appl. No. 12/958,302, filed Dec. 1, 2010 in the name of Tiziana C. Bond.
Non-Final Office Action mailed on Sep. 2, 2014 for U.S. Appl. No. 14/302,276, filed Jun. 11, 2014 in the name of Tiziana C. Bond et al.
Notice of Allowance mailed on May 5, 2014 for U.S. Appl. No. 12/958,302, filed Dec. 1, 2010 in the name of Tiziana C. Bond et al.
Final Office Action mailed on Jun. 19, 2014 for U.S. Appl. No. 13/117,079, filed May 26, 2011 in the name of Sonia Edith Letant et al.
Notice of Allowance mailed on Oct. 7, 2014 for U.S. Appl. No. 13/117,079, filed May 26, 2011 in the name of Sonia Edith Letant et al.
Non-Final Office Action mailed on Nov. 27, 2013 for U.S. Appl. No. 13/410,226, filed Mar. 1, 2012 in the name of Mihail Bora et al.
Notice of Allowance mailed on Mar. 17, 2014 for U.S. Appl. No. 13/410,226, filed Mar. 1, 2012 in the name of Mihail Bora et al.
Hirsch, L. R.; Jackson, J. B.; Lee, A.; Halas, N. J.; West, J., "A Whole Blood Immunoassay Using Gold Nanoshells", Analytical Chemistry 2003, 75, 2377-2381.
Rich, R. L. et al. "Advances in surface plasmon resonance biosensor analysis", Current Opinion in Biotechnology 2000, 11, 54-61.
Bora, M. et al., "Near field detector for integrated surface plasmon resonance biosensor applications", Optics Express 2009, 17, 329-336.
Barnes, W. L et al., "Surface plasmon subwavelength optics", Nature 2003, 424, 824-830.
Ghaemi, H. F. et al. "Surface plasmons enhance optical transmission through subwavelength holes", Physical Review B 1998, 58, 6779-6782.
Lezec, H. J. et al. "Beaming Light from a Subwavelength Aperture", Science 2002, 297, 820-822.
Morfa, A. J. et al. "Surface-plasmon enhanced transparent electrodes in organic photovoltaics", Applied Physics Letters 2008, 92, 243304-1-243304-3.
Tvingstedt, K. et al. "Surface plasmon increase absorption in polymer photovoltaic cells", Applied Physics Letters 2007, 91, 113514-1-113514-3.
Westphalen, M. et al. "Metal cluster enhanced organic solar cells", Solar Energy Materials and Solar Cells 2000, 61, 97-105.
Miyazaki, H. T. et al. "Controlled plasmon resonance in closed metal/insulator/metal nanocavities", Applied Physics Letters 2006, 89, 211126-1-211126-3.
Haynes, C. L.; Van Duyne, R. P., "Nanosphere Lithography: A Versatile Nanofabrication Tool for Studies of Size-Dependent Nanoparticle Optics", Journal of Physical Chemistry B 2001, 105, 5599-5611.
Haynes, C. L.; Van Duyne, R. P., "Plasmon-Sampled Surface-Enhanced Raman Excitation Spectroscopy", Journal of Physical Chemistry B 2003, 107, 7426-7433.
Michaels, A. M.; Nirmal, M.; Brus, L. E., "Surface-Enhanced Raman Spectroscopy of Individual Rhodamine 6G Molecules on Large Ag Nanocrystals", Journal of the American Chemical Society 1999, 121, 9932-9939.
Noginov, M.; Zhu, G.; Belgrave, A.; Bakker, R.; Shalaev, V.; Narimanov, E.; Stout, S.; Herz, E.; Suteewong, T.; Wiesner, U., "Demonstration of a spaser-based nanolaser", Nature 2009, 460, 1110-1113.
Zhang, S. et al "Surface plasmon resonance characterization of thermally evaporated thin gold films", Surf. Sci. 2007, 601, 5445-5458.
Manjavacas, A.; de Abajo, F. J. G., "Robust Plasmon Waveguides in Strongly Interacting Nanowire Arrays", Nano Letters 2009, 9, 1285-1289.
Manjavacas, A. et al. "Coupling of gap plasmons in multi-wire waveguides", Optics Express 2009, 17, 19401-19413.
Stegeman, G. I. et al. "Excitation of surface polaritons by end-fire coupling", Optics Letters 1983, 8, 386-388.
Dionne, J. A. et al. "Plasmon slot waveguides: Towards chip-scale propagation with sub-wavelength scale localization", Physical Review B 2006, 73, 035407, 1-9.
Lezec, H. J. et al. "Negative Refraction at Visible Frequencies", Science 2007, 316, 430-432.
Prodan, E. et al. "A Hybridization Model for the Plasmon Response of Complex Nanostructures", Science 2003, 302, 419-422.
Sun, Z. J. et al. "Coupling of Surface Plasmon Waves in Metal/Dielectric Gap Waveguides and Single Interface Waveguides", Journal of the Optical Society of America B—Optical Physics 2007, 24, 2883-2887.
Johnson, P. B. et al. "Optical Constants of the Noble Metals", Physical Review B 1972, 6, 4370-4379.
Notice of Allowance mailed on Mar. 4, 2004 for U.S. Appl. No. 10/159,175, filed May 31, 2002 in the name of Sonia Letant et al.
Non-Final Office Action mailed on Apr. 14, 2006 for U.S. Appl. No. 10/833,573, filed Apr. 27, 2004 in the name of Sonia Letant et al.
Final Office Action mailed on Mar. 9, 2006 for U.S. Appl. No. 10/833,573, filed Apr. 27, 2004 in the name of Sonia Letant et al.
Non-Final Office Action mailed on Sep. 29, 2005 for U.S. Appl. No. 10/833,573, filed Apr. 27, 2004 in the name of Sonia Letant et al.
Notice of Allowance mailed on Jul. 26, 2006 for U.S. Appl. No. 10/833,573, filed Apr. 27, 2004 in the name of Sonia Letant et al.
International Search Report mailed on Aug. 7, 2007 for International Patent Application No. PCT/FR2007/050868 filed on Mar. 1, 2007 (English Translation + French Original).
Written Opinion mailed on Aug. 7, 2007 for International Patent Application No. PCT/FR2007/050868 filed on Mar. 1, 2007.
International Preliminary Report on Patentability completed on Dec. 3, 2008 for International Patent Application No. PCT/FR2007/050868 filed on Mar. 1, 2007.

(56) References Cited

OTHER PUBLICATIONS

Lee, M.R. et al. "Two-dimensional silicon photonic crystal based biosensing platform for protein detection." Optics Express, 15(8), pp. 4530-4535, 2007.
Canham, L.T. "Silicon quantum wire array fabrication by electro-chemical and chemical dissolution of wafers." Appl. Phys. Lett., vol. 57, 1990, pp. 1046-1048.
Lehmann, V. et al. "Formation Mechanism and Properties of Electrochemically Etched Trenches in n-Type Silicon." J. Electrochem. Soc. vol. 137(2), pp. 653-659, 1990.
Birner, A. et al. "Silicon-Based Photonic Crystals." Adv. Mat. vol. 13(6), pp. 377-388, 2001.
Foresi, J.S. et al. "Photonic-bandgap microcavities in optical waveguides." Nature vol. 390, pp. 143-145, 1997.
Hsu, F. et al. "Growth of High-Density Titanium Silicide Nanowires in a Single Direction on a Silicon Surface." Nano Letters, vol. 7(4), pp. 885-889, 2007.
Segalman, R.A. "Patterning with block copolymer thin films." Mat. Sci. and Eng. R 48, pp. 191-226, 2005.
Fitz, J.L. et al., "Integrated Photonic Inverter with Gain." IEEE PTL, vol. 13(5), pp. 478-480, May 2001.
Vercoutere, W. et al "Rapid discrimination among individual DNA hairpin modecules at single-nucleotide resolution using an ion channel." Nature Biotechnology, vol. 19, pp. 248-252, Mar. 2001.
Jirage, K. et al. "Nanotubule-based Molecular-Filtration Membranes." Science, vol. 278, pp. 655-658, 1997.
Birner, A. et al. "Transmission of microcavity structure in a two-dimensional photonic crystal based on macroporous silicon" Materials Science in Semiconductor Processing 3, pp. 487-491 2000.
Blanco, A. et al."Large-scale synthesis of a silicon photonic crystal with a complete three dimensional bandgap near 1.5 micrometer." Nature 405, pp. 437-440, 2000.
Lehmann, V. "The Physics of Macropore Formation in Low Doped n-Type Silicon." *J. Electrochem. Soc.* 140(10), pp. 2836-2843, 1993.
Sigalas, M. et al. "Photonic band gaps and defects in two dimensions: studies of the transmission coefficient." *Phys. Rev. B* 48(19), pp. 14121-14126 (1993).
McCall, S.L. et al. in "Microwave propagation in two-dimensional dielectric lattices." Phys. Rev. Lett. vol. 67(15), pp. 2017-2020 (1991).

Janshoff, A. et al. "Macroporous p-type silicon Fabry-Perot layers. Fabrication, characterization, and applications in biosensing," *J. Am. Chem. Soc.* 120, pp. 12108-12116 (1998).
Buriak, J.M. et al. "Lewis acid mediated hydrosilylation on porous silicon." *J. Am. Chem. Soc.* 121, pp. 11491-11502 (1999).
Dancil, K.P. et al, "A Porous Silicon Optical Biosensor: Detection of Reversible Binding of IgG to a Protein A-Modified Surface," J. *Am. Chem. Soc.* 121, pp. 7925-7930, 1999.
Boukherroub, R. et al. in "Thermal hydrosilylation of undecylenic acid with porous silicon", Journal of The Electrochemical Society, vol. 149(2), H59-H63 (2002).
J.O. Smith III, "Viewpoints on the History of Digital Synthesis." Proceedings of the International Computer Music Conference (ICMC-91, Montreal). pp. 1-14, Dec. 28, 2005.
A.C. Denbrinker et al. "Parametric coding for High-Quality Audio" 112th AES convention, Munich, Germany. 10 pgs. May 10-13, 2002.
Szczerba, M., et al. "Parametric Audio Coding Based Wavetable Synthesis." 116th AES convention, Berlin, Germany. 6 pgs. May 8-11, 2004.
J. Daniel "Spatial Sound Encoding Including Near Field Effect: Introducing Distance Coding Filters and a Viable, New Ambisonic Format." AES 23$^{rd}$ International Conference, Copenhagen, Denmark. 15 pgs. May 23-25, 2003.
G. Pallone Dilatation et transposition sous contraintes perceptives des signaux audio: Application au transfert cinema-video. 250 pgs. 2003.
Notice of Allowance for U.S. Appl. No. 12/225,097, filed Oct. 24, 2008 in the name of Gregory Pallone et al. mailed on Sep. 12, 2011.
Non-Final Office Action issued for U.S. Appl. No. 14/302,276, filed Jun. 11, 2014 in the name of Tiziana C. Bond et al. Mail Date: Dec. 4, 2014.
Notice of Allowance issued for U.S. Appl. No. 14/302,276, filed Jun. 11, 2014 in the name of Tiziana C. Bond et al. Mail Date: Mar. 16, 2015.
Non-Final Office Action for U.S. Appl. No. 14/316,024, filed Jun. 26, 2014 in the name of Tiziana C. Bond et al. mailed on Aug. 15, 2014.
Restriction Requirement mailed on Jan. 9, 2013 for U.S. Appl. No. 12/957,883, filed Dec. 1, 2010 in the name of Lawrence Livermore National Laboratory.
Notice of Allowance for U.S. Appl. No. 12/957,883, filed Dec. 1, 2010 in the name of Tiziana Bond mailed on Mar. 18, 2014.

\* cited by examiner

Mounting of fiber in ferrule onto spin coater chuck.

NANOSCALE STRUCTURES ON OPTICAL FIBER FOR SURFACE ENHANCED RAMAN SCATTERING AND METHODS RELATED THERETO

CROSS REFERENCE TO RELATED APPLICATIONS

The present application claims priority to U.S. Provisional Application 61/691,036, filed on Aug. 20, 2012, which is incorporated herein by reference in its entirety. The present application may be related to U.S. Pat. No. 8,059,924 entitled "Multiplexed Photonic Membranes and Related Detection Methods for Chemical and/or Biological Sensing Applications", granted on Nov. 15, 2011, U.S. application Ser. No. 12/958,302 entitled "Methods and Systems for Raman and Optical Cross-Interrogation in Flow-Through Silicon Membranes", filed on Dec. 1, 2010, U.S. application Ser. No. 13/117,079 entitled "Methods for Isolation and Viability Assessment of Biological Organisms", filed on May 26, 2011, U.S. application Ser. No. 12/957,883 (US 2011/0128536 A1) entitled "Nanoscale array structures suitable for surface enhanced Raman scattering and methods related thereto", filed on Dec. 1, 2010, and U.S. application Ser. No. 13/410,226, filed on Mar. 1, 2012, entitled "Plasmon resonant cavities in vertical nanowire arrays", the disclosure of each of these references being incorporated herein by reference in their entirety.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
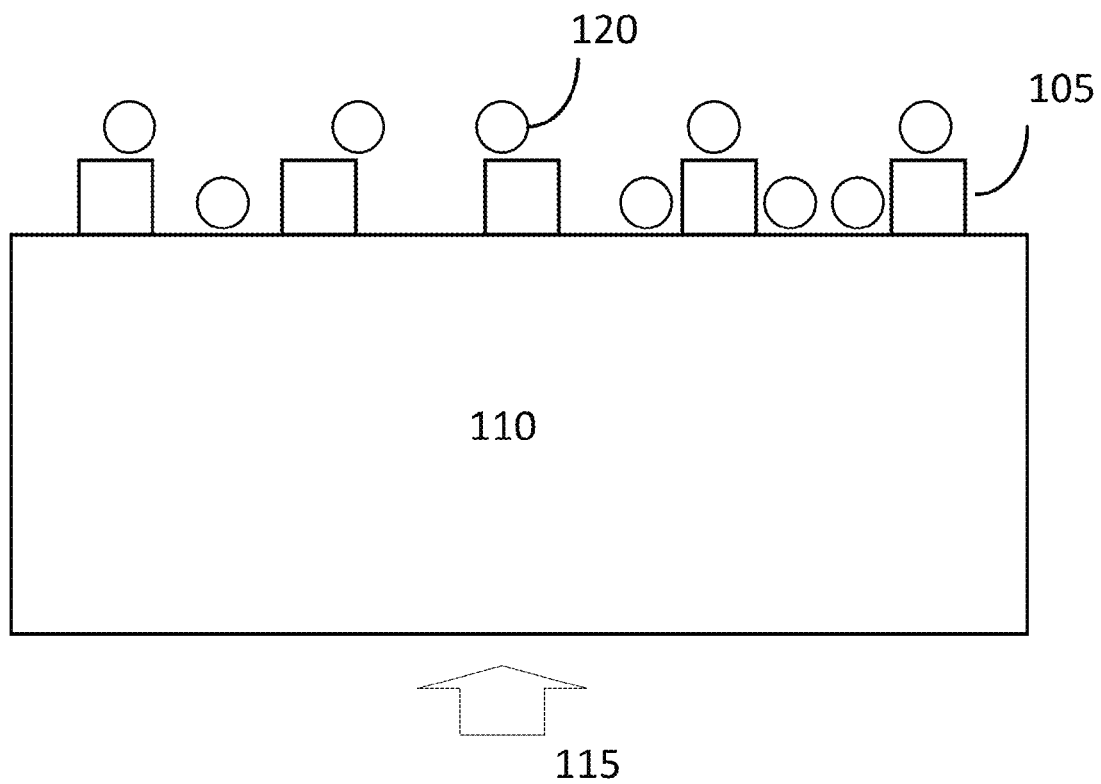
FIG. 1 depicts a schematic of an array structure on an optical fiber for surface-enhanced Raman scattering.

According to a first aspect, a structure for detecting molecules is provided, comprising: a planar facet end of an optic fiber; a nanoscale structure on the planar facet end; a metal covering the nanoscale structure.

DETAILED DESCRIPTION

Raman scattered light is considered a chemical signature of chemical and biological molecules since all molecules with unique chemical compositions have unique Raman scattering spectra. Raman scattering spectroscopy is thus a powerful technique to detect chemical and biological molecules without labeling and has potential applications in high-sensitivity detections of explosives, pathogens, and contaminants in the field. Unfortunately, Raman scattering is an extremely inefficient process due to its weak sensitivity as compared to other scattering mechanisms—roughly only 1 in $10^8$ photons ends up in Raman scattering (Jarvis and Goodacre, 2004 *Anal. Chem* 76 40)—and also due to typical lower scattering cross-sections of the Raman process (about $10^{-30}$ cm$^2$), which is around 15 orders of magnitude lower than fluorescence emission (Vo-Dinh et al., 2002 *J. Raman Spectrosc.* 33 511). In order to get a detectable Raman scattering signal, it is necessary to use an array of filtering techniques or to enhance the Raman scattering process. The latter of the two can be achieved using surface enhanced Raman scattering, which is also known as surface enhanced Raman scattering spectroscopy or surface enhanced Raman spectroscopy. For the sake of clarity, throughout the present disclosure, the term "SERS" intends to indicate surface enhanced Raman scattering.

Surface-enhanced Raman scattering (SERS) is a powerful spectroscopic technique for molecular detection due to its high sensitivity and molecular specificity. SERS can provide a nondestructive and ultrasensitive detection technique which is effective down to a single-molecule level. SERS is able to give a molecular "fingerprint" information with high sensitivity. As part of the standard set-up for this technique, optical fibers have been used as SERS probes because of their low cost, flexibility, compactness, and remote sensing capability. In the present disclosure, fabricating a nanoscale structure on a facet end of an optical fiber enables the nanoscale structure to be used as a probe to detect molecules by surface-enhanced Raman scattering. The close integration of the optical fiber with the nanoscale structure may include several advantages, one being an enhancement in detection of the SERS signal.

The nanoscale structure may be fabricated by different methods, and may comprise a periodic array, such as an array of nanopillars; it may also comprise a non periodic, or even random, surface-relief pattern. The longitudinal axis of the periodic array, or the average vector of the longitudinal axis in a random relief pattern, may be substantially aligned to the longitudinal axis of the optical fiber. For example, the axis of an array of nanopillars may be aligned to the longitudinal axis of the optical fiber. As another example, if the surface-relief pattern comprises a number of irregular, elongated, ellipsoidal shapes, such shapes might be randomly aligned (or non aligned) to each other, or they might be elongated approximately in the same direction. The average direction of such random relief patterns, or of regular, periodical arrays such as an array of nanopillars, may also be aligned at a specific angle to the longitudinal axis of the optical fiber, depending on the requirements of a specific set-up used to detect specific molecules by SERS.

An example of a random surface-relief pattern that may be fabricated on an optical fiber for SERS application can be found in Hobbs (U.S. Pat. No. 8,187,481 B1), incorporated herein by reference in its entirety. Hobbs describes a surface-relief structure consisting of a random distribution of surface features with varying feature profile and depth. The random texture of Hobbs suppresses reflection of electromagnetic waves. A similar relief pattern, if coated with a metal layer and fabricated on an optical fiber, might enable surface enhanced Raman scattering with, for example, better signal-to-noise ratios, as it could decrease unwanted reflection of the incident light used in the SERS detection technique. In general, any method that can be used to create a 'moth's eye' or nanoscale antireflection surface structure on a fiber facet may also be used to create similar features that may be suitable for SERS devices when coated with a metal film.

An example of a fabrication technique to be used for realizing nanoscale structures for SERS detection might include, in one embodiment, the application of interference lithography, enabling fabrication of a periodic array structure on an optic fiber, which can be used as a probe to detect molecules by surface-enhanced Raman scattering. Interference lithography, as known by those skilled in the art, is the creation of an interference pattern with a single source of light (whose beam can be divided into at least two beams) or with at least two sources of light. An example of a source of coherent light for interference lithography might be a laser.

FIG. 1 depicts a schematic cross sectional point of view of one embodiment of the present disclosure, where a number of periodically spaced elements (105) forms an array structure, the structure fabricated on one end of an optical fiber (110). The spacing between pillars could be adjusted for optimal SERS detection; for example, it could be about 300 nm. By way of example and not of limitation, in one embodiment the optical fiber conveys the light of a laser (115) from the optic fiber towards the array structure at the tip of the optic fiber, and also in the opposite direction, away from the array structure and into the optic fiber. In one embodiment, the array structure is formed by a number of nanopillars with axis parallel to each other. The axis of each nanopillar is substantially aligned with the longitudinal axis of the optical fiber. The nanopillars may be of the same material of the optic fiber (for example, obtained by etching the fiber), or they may be of a different material. In another embodiment, the nanopillars may be of the same material of the optic fiber, and coated with a different material, for example a metal.

In one embodiment, the nanopillars are fabricated by interference lithography, through the use of coherent light creating interference patterns onto a photoresist. By way of example and not of limitations, some exemplary methods of fabrications for array structures suitable for SERS are described in a previous disclosure (US 2011/0128536, incorporated herein by reference in its entirety).

Figure 2A:
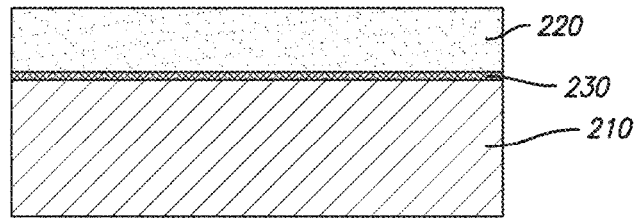
FIG. 2A depicts an optical fiber coated by an antireflective layer and a photoresist.

Referring now to FIG. 2A, in one embodiment of the present disclosure a method is provided to fabricate an array structure at an end facet of an optical fiber. First, an optical fiber is provided, suitable for a SERS measurement; for example, a standard silica multimode optical fiber can be used. One end facet of the optical fiber (210) is covered in an antireflection coating (230), an advantage of the coating (230) being to limit unwanted back-reflection. Such coating might be applied, for example, by spin coating, a method well known to those skilled in the art. The antireflective layer (230) is an optional layer which serves to improve the effective resolution of the photoresist layer (220) interaction with the light source by reducing or removing the reflection from the substrate (210). Then a photoresist (220) is deposited on the antireflective coating (230). Several standard methods exist to apply photoresist to a surface, for example nozzle spraying or spin coating; in one embodiment, spin coating is used to apply the photoresist (220).

Figure 2B:
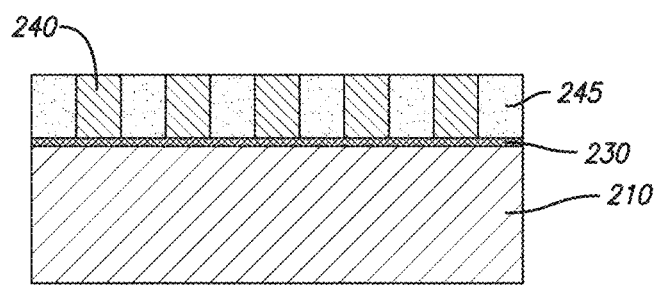
FIG. 2B depicts an optical fiber coated by an antireflective layer and a photoresist exposed to interference lithography laser light.

The photoresist (230) is subsequently defined by interferometrically-arranged laser beams, forming an array pattern on the photoresist (220). Photolithography techniques are well known in the art and might include several substeps; for example, the photoresist layer might actually be composed of two different photoresist layers. FIG. 2B depicts the result of the interference lithography step which creates an array pattern, prior to the development of the photoresist. Development is a standard process well known as such to those skilled in the art, typically consisting of a solution designed to wash away selected parts of the photoresist. After the photolithography light exposure by the interferometrically-arranged laser beams, some parts of the photoresist (240) become more resistant to development and other parts of the photoresist (245) become less resistant. For example, the parts (240) might be crosslinked while the parts (245) might not.

Figure 2C:
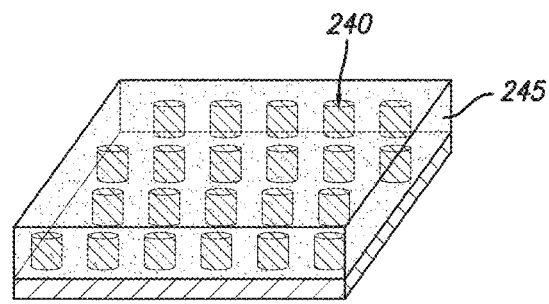
FIG. 2C is a perspective view of a pattern of nanopillars defined on an optic fiber coated in photoresist.

FIG. 2C depicts a perspective view of FIG. 2B, showing a pattern for an array of nanopillars, with parts (240) of the photoresist more resistant to development, and parts (245) of the photoresist less resistant to development.

Figure 2D:
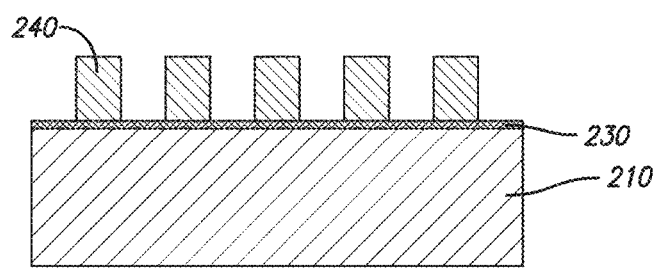
FIG. 2D depicts an optical fiber coated by an antireflective layer and a photoresist after the photoresist has been developed.

In a next step, depicted in FIG. 2D, the photoresist is developed, leaving a photoresist array of nanopillars (240), on top of the antireflection coating (230) and the optical fiber (210).

Figure 2E:
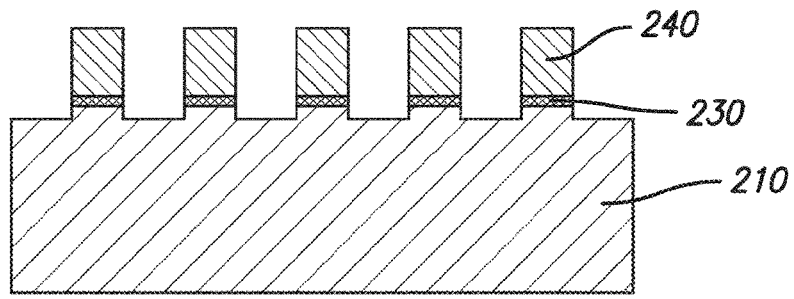
FIG. 2E depicts an optical fiber coated by an antireflective layer and a photoresist during a removal step of the fabrication.

Subsequently, as depicted in FIG. 2E, the antireflective coating (230) and the portion of the optical fiber (210) adjacent to the antireflective coating are partially removed by a removal process such as ion milling, reactive ion etch, or wet etch. The parts of the optical fiber (210) and of the antireflective coating (230) covered by the array of photoresist pillars (240) are protected while the exposed parts of the planar substrate (210) and of the antireflective coating (230) are removed.

Figure 2F:
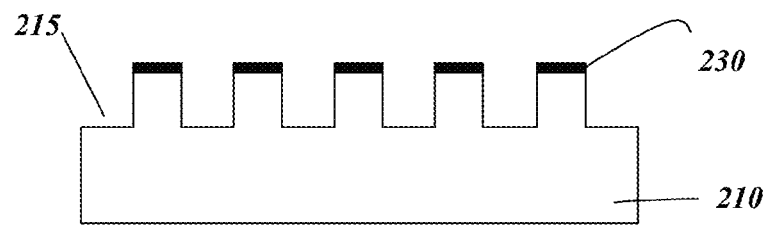
FIG. 2F depicts an optical fiber coated by an antireflective layer during a removal step of the fabrication.
Figure 2G:
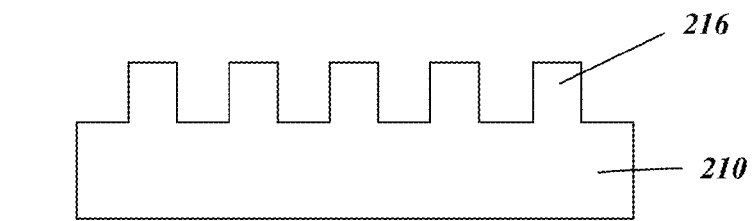
FIG. 2G depicts an optical fiber with an array of nanopillars having been etched on the surface.

As depicted in FIG. 2F, by continuing the removal process, the photoresist (240 in FIG. 2E) is completely removed and only the antireflective coating (230) and the end facet of the optical fiber (210) remain. During the removal process, portions of the upper surface (215) of the optical fiber (210) are removed as well. As the removal process continues longer still, the antireflective coating (230) is removed completely, and only the optical fiber (210) remains, as depicted in FIG. 2G. In FIG. 2G, an array of nanopillars (216), made entirely of the material of the optical fiber (210), is now present.

Figure 2H:
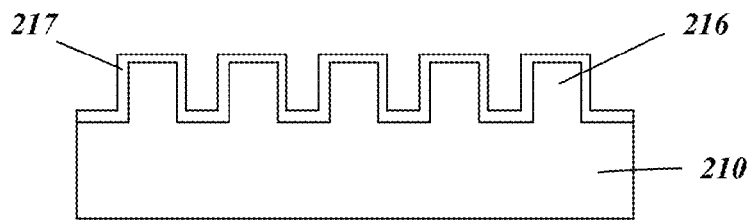
FIG. 2H depicts a metal coating on a nanopillars array on an optical fiber.

As depicted in FIG. 2H, in a further step a layer of metal (217) is deposited onto the array of nanopillars (216) on the optical fiber (210). By way of example and not of limitation, silver might be deposited by e-beam on the nanopillars (216). The metal coverage of the nanopillars (216) might not be complete. The metal layer of FIG. 2H is intended as an example. Due to the fabrication process, or because of a deliberate choice to enhance the SERS signal, the metal might be covered at angle to the longitudinal axis of the nanopillars, thereby more metal might be present on one side of the pillars, relative to the other side, or the metal layer might not be continuous. For example, little to no metal might be present on certain or all sides of the nanopillars. As a further example, little to no metal might be present on the surface of the optical fiber between the nanopillars.

By way of example and not of limitation, the metal coating can be selected from the group consisting of: silver, gold, aluminum, iridium, platinum, palladium and copper.

Figure 3:
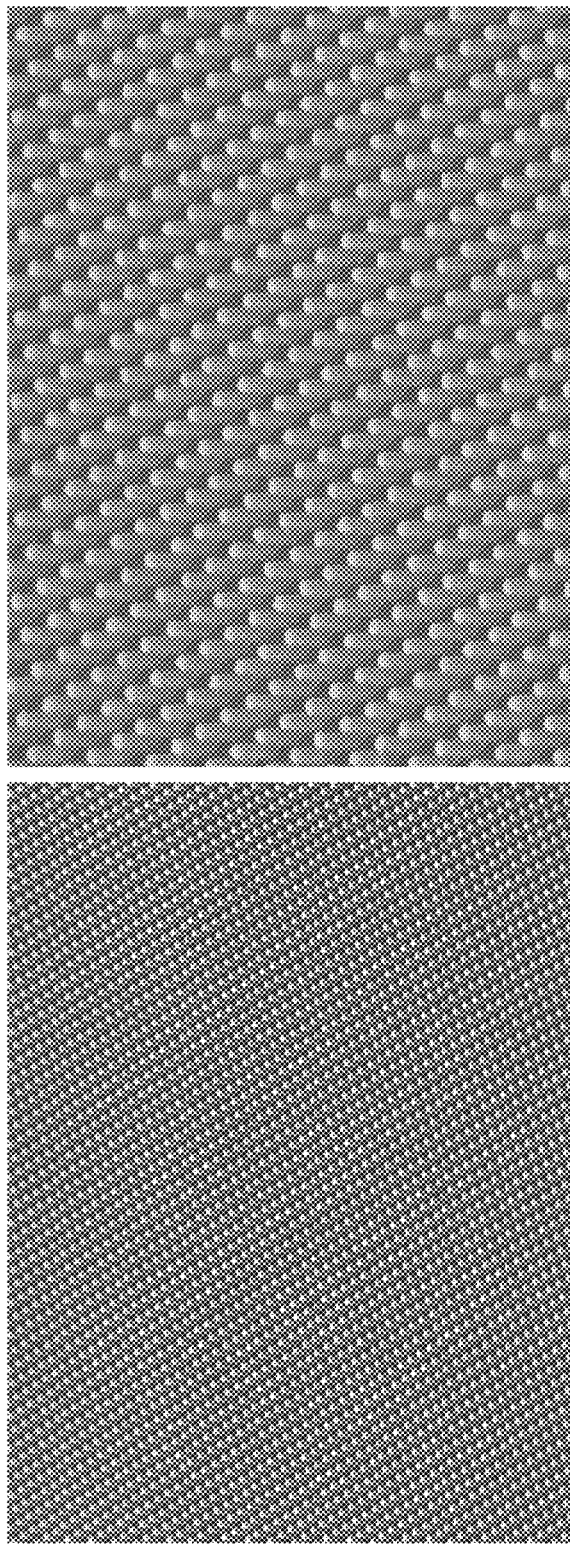
FIG. 3 depicts an SEM picture of an array nanostructure of nanopillars at two different magnifications.

FIG. 3 depicts two scanning electron microscope (SEM) pictures, at different levels of magnifications, of an embodiment of the present disclosure, where the array is formed by nanopillars patterned onto an optic fiber.

Figure 3A:
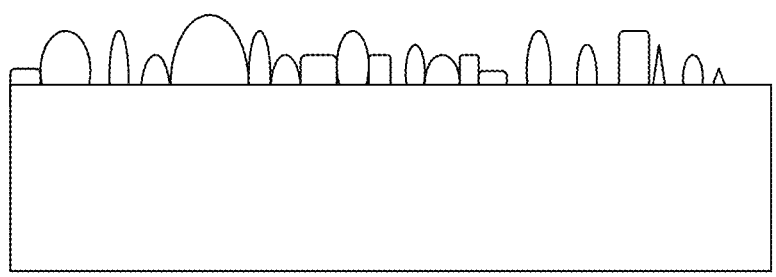
FIG. 3A depicts an example of a non periodic relief structure.

FIG. 3A depicts an example of an embodiment of the disclosure with a random surface-relief pattern.

Referring now again to FIG. 1, the optical fiber (110), whose end facet has, in this embodiment, an array of nanopillars (105) (which may be coated in metal), can be used as a sensing probe to detect the presence of molecules (120), both chemical and biological. The sensing is carried out through surface-enhanced Raman scattering. Typically, the molecules (120) are adsorbed onto the surface. By way of example and not of limitations, a trans-1,2-bis(4-pyridyl)-ethylene (BPE) monolayer could be detected by the sensing probe. In another example, toluene vapor could be detected. Both examples have been described as such in a previous disclosure, X. Yang et al., Optics Express, Vol. 20, Issue 22, pp. 24819-24826 (22 Oct. 2012), which is incorporated by reference herein in its entirety, and referred to from now on as Yang.

To build a highly integrated optical SERS sensing system for practical applications, it is desirable to fabricate the SERS substrate on the facet of an optical fiber. The main challenge during fabrication is how to control the position and orientation of the fiber tip in the processes of spin coating, lithography, etching, and vapor deposition, such as those described in one embodiment of the present disclosure (in FIGS. 2A-2H), as the fiber has a small diameter and a large aspect ratio. For example, the optical fiber used in Yang had a 50 μm core diameter and a 125 μm cladding diameter, while a typical length was 10 cm.

Figure 4:
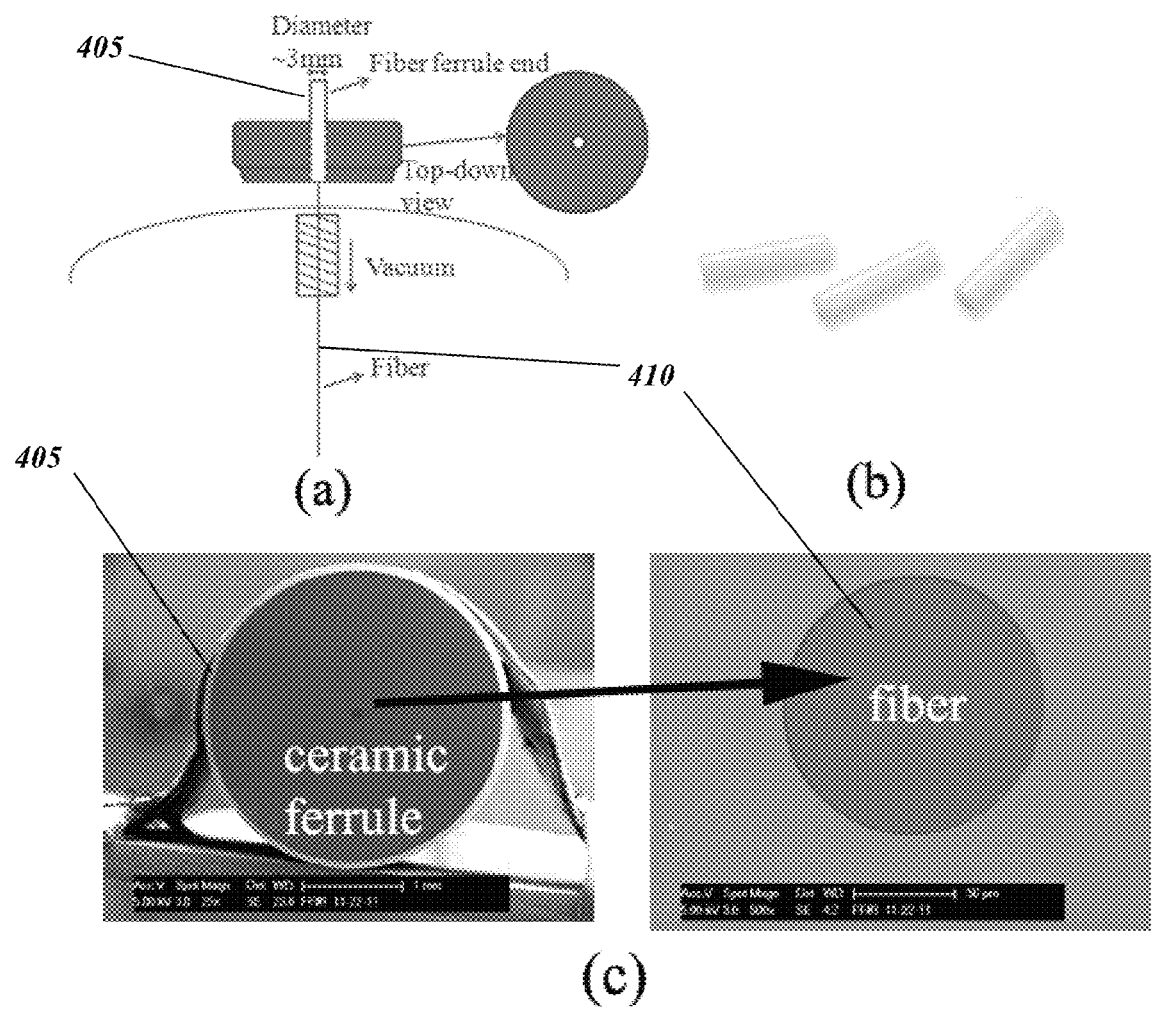
FIG. 4 depicts a ceramic ferrule attached to an optical fiber.

As depicted in FIG. 4, a ceramic ferrule (405) can be attached at one end of the fiber (410) for processing and fabrication of the nanoarray. FIG. 4 includes an SEM image of the ceramic ferrule (405) and the optical fiber (410).

As described in Yang, as an example embodiment of the present disclosure, a standard silica multimode optical fiber (OFS Fitel, LLC., model: BF06864, NA=0.22), with a 50 μm core diameter and a 125 μm cladding diameter, was attached to a custom-made ceramic ferrule. The fiber facet with the fiber ferrule was first spin coated with a 260 nm thick antireflection layer and then coated with a 700 nm thick photoresist. The nanopillar array was then fabricated onto the fiber facet by interference lithography by laser light. The laser wavelength for interference lithography was 413 nm and the dose was around 80 mJ/cm$^2$. The resultant photoresist pattern was a two-dimensional periodic nanopillar array with a 317 nm pitch and a 160 nm pillar diameter. An ion milling deep reactive ion etching step was used to remove the antireflection layer between the photoresist nanopillars (mask), after which the unprotected silica area was etched down to 600 nm and then the residual photoresist mask on the top of the nanopillars was washed away. Finally a 60 nm layer of silver was e-beam evaporated at a deposition rate of 0.1 nm/s onto the fiber facet at an angle of 60° to make it SERS-active. Experimentally, several deposition angles (relative to the longitudinal axis of the fiber) for the e-beam were tested, such as 0°, 30°, and 60°. In Yang, the 60° deposition angle resulted in the best SERS signal, however it will be obvious to those skilled in the art that the optimal deposition angle might vary depending on different factors, for example (and not limited to) the set-up configuration, the materials used, and the specific molecules to be detected. The present disclosure is not intended to be limited to any one specific angle of deposition for the metal layer.

Those skilled in the art will realize that different types of nanostructures could be fabricated, and the described embodiment is meant to provide an example and clarify the intended scope of the present disclosure, and is not intended as a limitation. For example, the method of using a ceramic ferrule for fabricating a nanostructure on the optical fiber is not limited to fabricating periodic structures such as the array of nanopillars, but may be used for other embodiments, with different fabrication techniques and different nanoscale structures.

In one embodiment, the size, gap width and height of the array of nanopillars are configured to enable surface enhancement of Raman scattering.

In another embodiment, the structure is comprised of nanorecesses. In yet another embodiment, the antireflection coating could be absent. The interferometry-lithography technique is intended as an exemplary technique of fabrication. Those skilled in the art will realize that a different technique of fabrication is intended to be within the scope and application of the present disclosure. In another embodiment, the antireflective coating and/or the metal coating layers are not continuous.

Figure 5:
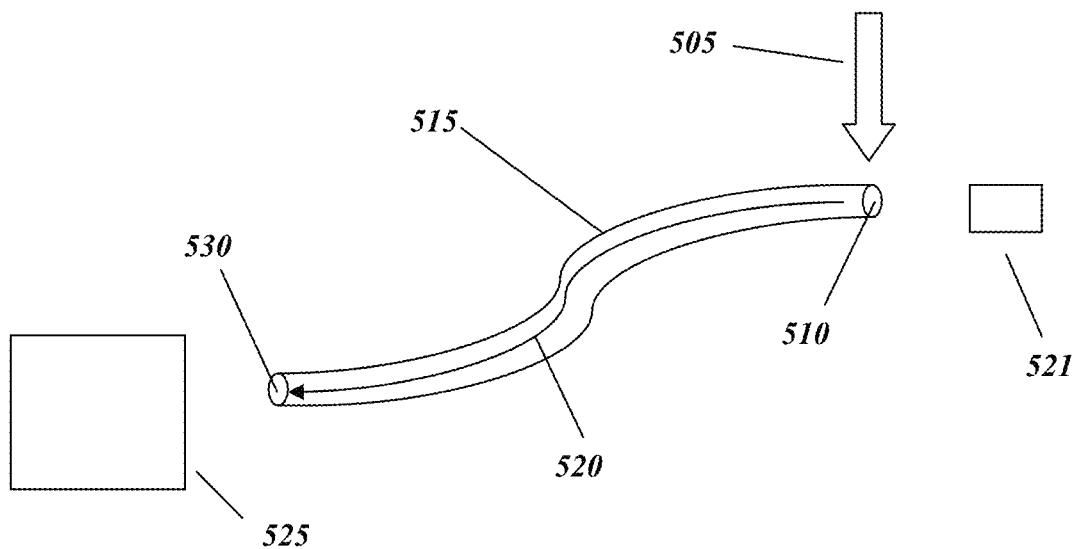
FIG. 5 depicts a front end detection configuration.

By way of example and not of limitation, for a SERS measurement using an array structure of the present disclosure, two exemplificatory configurations could be used. Referring to FIG. 5, a first configuration is denoted front end detection, in which a laser light (505) is focused directly by an objective lens onto the patterned fiber facet (510) (the facet with the nanoarray) of the optical fiber (515). A SERS signal (520), caused by the interaction with the molecules in the sample holder area (521), is collected via a backscattering geometry by the sensing apparatus (525) at the opposite, unpatterned, fiber facet (530).

Figure 6:
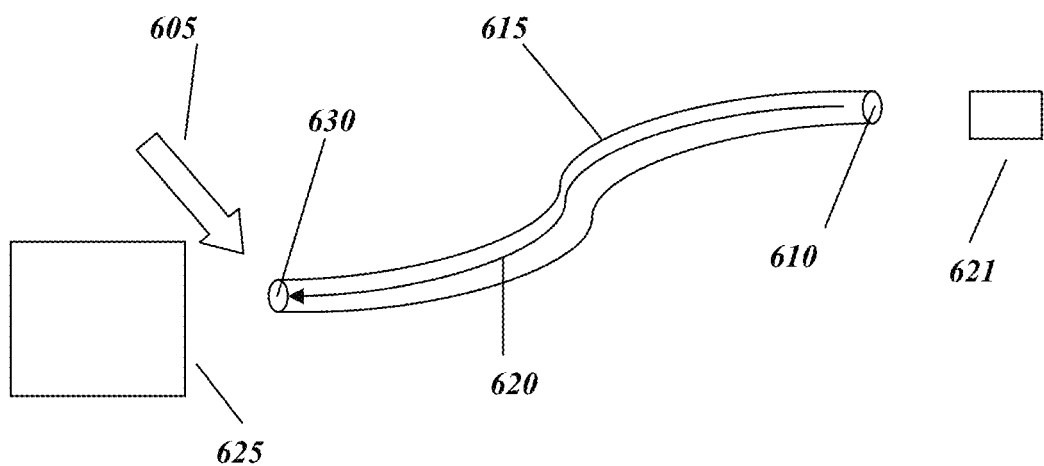
FIG. 6 depicts a remote end detection configuration.

Referring to FIG. 6, a second configuration is denoted remote end detection, in which the laser light (605) is coupled with the unpatterned fiber end (630) of the optical fiber (615). The laser light is propagated through the fiber to the remote patterned facet (610), and triggers a SERS signal (620) at the remote patterned facet (610) which is propagated back to the unpatterned end (630). In this second configuration, a SERS signal (620), from the molecules in the sample holder area (621), is collected from the distal (patterned) fiber end (610) and coupled back to a sensing apparatus (625) (for example, a Raman spectrometer) at the unpatterned facet (630) of the optic fiber (615).

In another aspect of the present disclosure, the optical fiber sensing probe, for example that of the embodiments described in FIG. 1, is characterized by a method using a front end detection, the method comprising focusing laser light onto the array of nanopillars, which constitutes a surface-enhanced Raman scattering (SERS) probe. As the focused laser light is backscattered, the method further comprises collecting a SERS signal via a backscattering geometry and estimating an enhancement factor based on the front end detection technique, enabling a comparison between the standard Raman detection technique, and SERS technique.

In one embodiment of the characterization method, the enhancement factor (EF) is calculated using the follow expression:

$$EF = \frac{I_{SERS}\, P_{Raman}\, N_{Raman}\, P_{Raman}}{I_{Raman}\, P_{SERS}\, N_{SERS}\, P_{SERS}}$$

where $I_{SERS}$ is the SERS intensity, $I_{Raman}$ is the Raman intensity; $P_{SERS}$ and $P_{Raman}$ are the laser power for SERS measurement and Raman measurement respectively; $T_{SERS}$ and $T_{Raman}$ are the integration time for SERS measurement and Raman measurement respectively; $N_{SERS}$ and $N_{Raman}$ are the number of molecules involved for SERS measurement and Raman measurement, respectively. As described in a previous disclosure, X. Yang et al., Optics Express, Vol. 20, Issue 22, pp. 24819-24826 (22 Oct. 2012), an enhancement factor $EF=1.2\times10^7$ has been measured for the nanostructure of FIG. 3.

Generally, the remote end configuration is more useful in sensing applications, while characterization from the front end configuration provides a more direct measurement of the enhancement factor (EF) of the SERS substrate itself to give an indication of the quality and performance of the substrate. The present disclosure, however, is not intended to be limited to the front end or remote end configurations, as either could be used for any purpose, and another possible configurations might be used as well.

During fabrication of a nanostructure on an optical fiber it may be challenging to perform several of the fabrication steps, for example fixing an optical fiber on a spin coater, or keeping its longitudinal axis perpendicular to the photolithographic sources of light. In one embodiment of the present disclosure, a method is provided to fabricate a nanostructure on an optical fiber.

Figure 7:
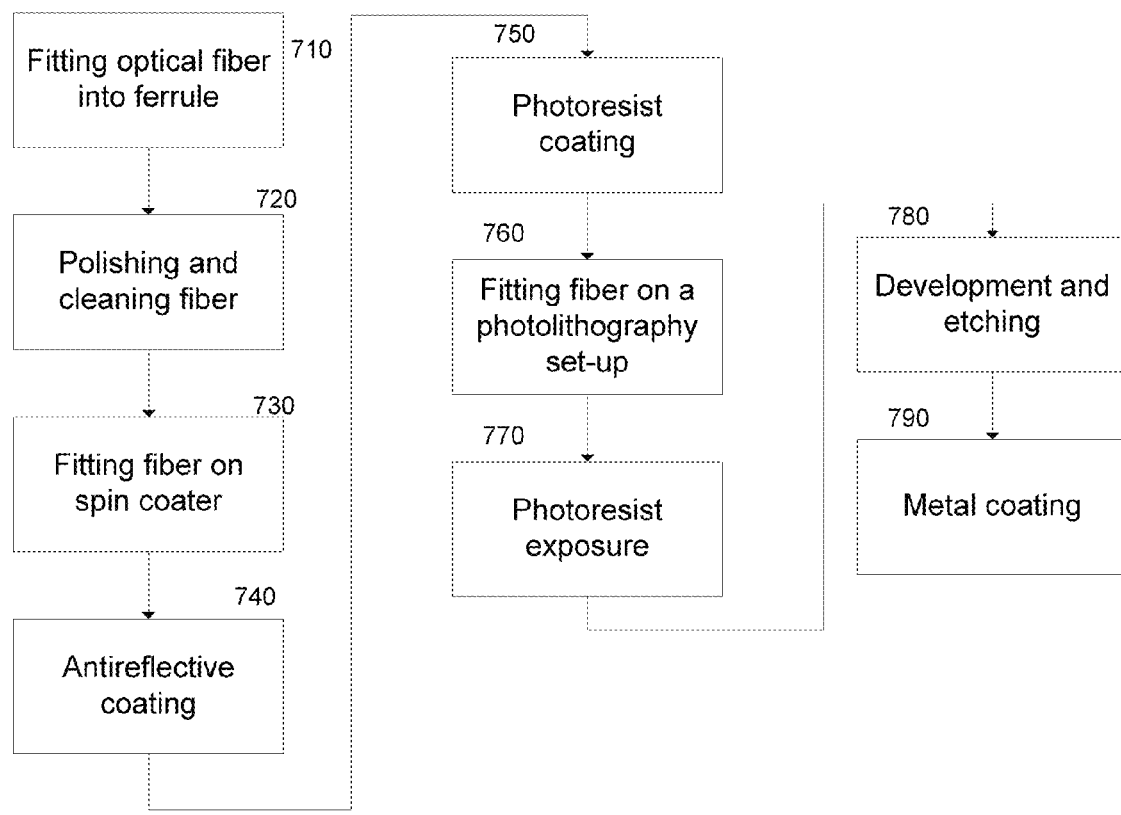
FIG. 7 depicts steps to fabricate an array structure on an optical fiber by lithography.

As shown in FIG. 7, an exemplary method comprises several steps. First, a standard optical fiber is obtained and the fiber is potted into a ferrule (710), using epoxy, for example, and the fiber facet polished and cleaned (720) along with the ferrule. A purpose of the polishing and cleaning step (720) may be to obtain a clean and flat surface, in order to evenly apply any necessary coating as well as limit light scattering by imperfections, during subsequent lithographic steps.

Figure 8:
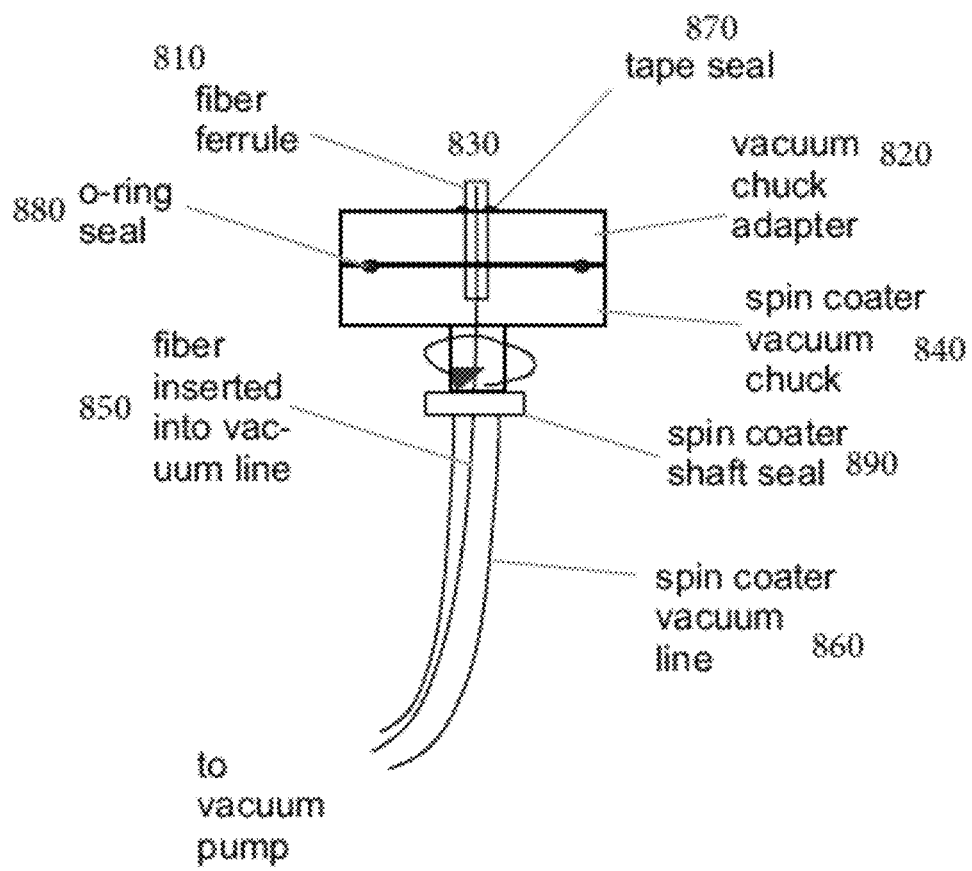
FIG. 8 depicts an optical fiber and ferrule attached to a spin coater chuck.

Next, the optical fiber with the ferrule can be fitted on a spin coater (730) as shown in FIG. 8.

This step (730) is described in detail referring to FIG. 8: the fiber end with the ferrule (810) can be press-fitted onto an adapter (820) such that the end to be coated (830) protrudes from the adapter (820). The assembly comprising the fiber and ferrule (810) and the adapter (820) can be mounted on a spin coater chuck (840) in such a way that the remaining part of the fiber (850) is inserted into the hollow shaft in the chuck which is also the vacuum supply line (860). Tape (870) can be used to make a vacuum-tight seal between the ferrule (810) and the hole in the adapter (820). An O-ring (880) can ensure a vacuum seal between the vacuum chuck adapter (820) and the vacuum chuck (840). There may also be a shaft seal (890) to seal the vacuum line (860).

Referring back to FIG. 7, a layer of absorbing (anti-reflective) film can be applied (740) to the fiber facet fitted to the spin coater. The application step (740) of the film may comprise, for example, spinning on the film, dismounting the fiber/ferrule assembly and curing the film by baking. This film can reduce back scattering during subsequent lithography steps. The fiber/ferrule assembly can be then be fitted again on the spin coater. Subsequently (750) a photoresist layer can be applied. The application step (750) for the photoresist may comprise, for example, spinning on the photoresist, dismounting the fiber/ferrule assembly and curing the photoresist by softbaking. Those skilled in the art will realize that a different coating procedure may be used, such as nozzle spraying.

Those skilled in the art will know that standardized film thickness for spun-on layers is normally provided, depending on several parameters, for example the rotational speed of a spin coater. However, due to the unique set-up required to apply the films on a fiber facet, it may be advantageous to measure the thickness of the film, as the expected, standardized film thicknesses may not be correct. The film thickness may be important, as known in the art, when determining the amount of irradiation needed during photolithography. Thickness calibration with samples of the same form factor may be required to determine the thickness of the applied and baked film layers. Measurement of film thickness was very challenging given the small diameter of the fiber in the center of the ferrule. To ensure a correct calibration, Focused Ion Beam (FIB) milling was used to remove a portion of the film layers so that scanning electron microscopy (SEM) could be employed to measure the film thickness.

In the next step the optical fiber is fitted onto a photolithographic set-up (760) and subsequently the photoresist is exposed (770) to obtain a photolithographic pattern on the fiber end coated in photoresist. Steps (760) and (770) may be carried out, for example, by standard laser interference lithography methods by exposing the fiber end coated in photoresist to interfering beams from a coherent laser source of wavelength $\lambda$ incident on the fiber face at angle $+/-\theta$, generating a latent grating with period $d=\lambda/[2 \sin(\theta)]$. An exemplary setup is shown in FIG. 9.

Figure 9:
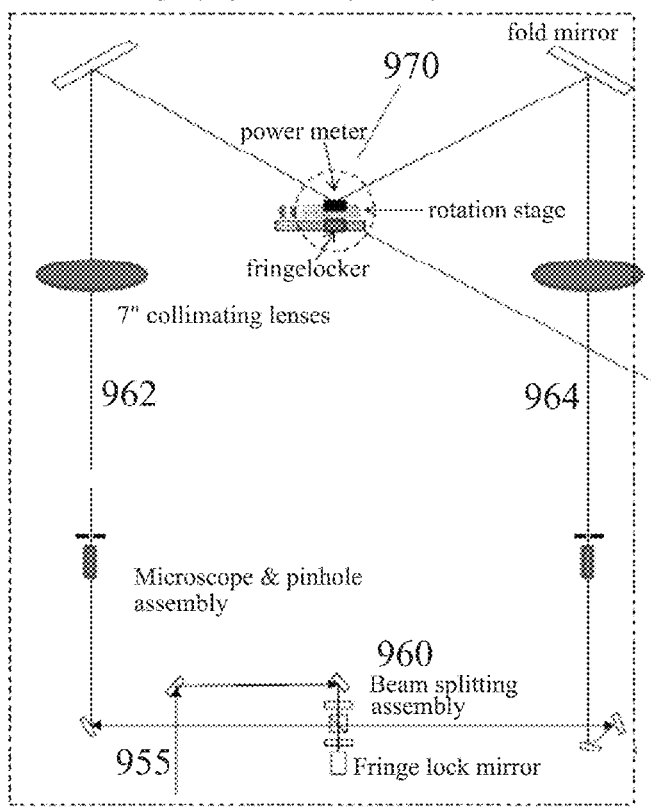
FIG. 9 depicts an optical fiber fitted to a photolithographic set-up.
Figure 9:
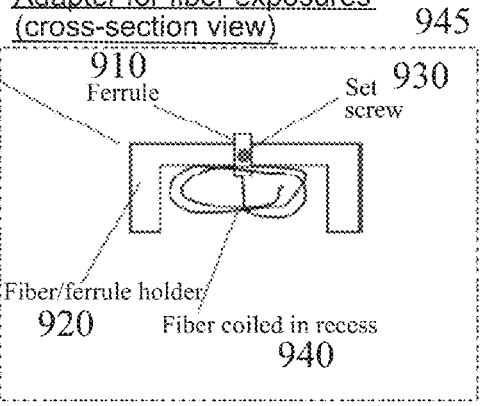

Referring to FIG. 9, in one embodiment the fiber/ferrule (910) can be fitted on a holder (920) with a screw (930). The remaining part of the fiber (940) is coiled into the hollowed-out recess on the back side of the holder (920). The fiber and holder assembly (also called adapter) (945) is then fitted onto the photolithographic set-up (950).

The photolithography set-up of FIG. 9 comprises a laser beam (955) which is splitted (960) into two beams (962, 964). The two beams converge onto the fiber/ferrule (910) fitted onto the adapter (945). Standard optical elements may be used as part of the photolithographic set-up, such as collimating lenses and mirrors.

After exposure of the photoresist a latent grating pattern of parallel lines is present into the photoresist layer on the fiber face; the adapter (945) is then rotated 90 degrees and another exposure carried out, to write a latent grating orthogonal to the first. The intersection of the nulls of the interference fields generates a periodic two-dimensional pattern (such as that of FIG. 2C). In other words, the intersection of the two orthogonal grating patterns of parallel lines defines a periodic pattern which can used to create nanopillars in the subsequent steps. This concludes step (770) of FIG. 7.

Referring back to FIG. 7, the next step is development and etching (780). The intersection of the nulls of the interference fields during exposure (770) has generated a periodic two-dimensional pillar array in the positive photoresist after the development step (780). Development can be carried out with a liquid base solution. In one embodiment, the periodic pattern can be transfer-etched into the silica fiber face first by etching through the absorbing layer, then etching into the bulk material of the fiber facet to the desired depth (see FIG. 2E). The photoresist and absorbing layer can be chemically removed, concluding the development and etching step (780) of FIG. 7.

In the last step (790), the periodic pillar array on the fiber end can be overcoated with metal (see FIG. 2H). Those skilled in the art will realize that the listed steps are exemplificatory and that different variations may be employed according to the present disclosure. For example, a different method to apply the photoresist (750) or the antireflective coating (740) may be employed (such as nozzle spraying). Similarly, a different lithographic technique may be used in (760,770), and the pattern of exposed photoresist may be non periodic or random.

During exposure of the photoresist in (770), it may be desirable to avoid back reflection from the optical fiber onto the photoresist; that may be an advantage provided by the antireflective coating (740, and 230 in FIG. 2A). Another way to reduce back reflection may be to bend, with a small bending radius, the part of the optical fiber which is not fitted to the ferrule (940 in FIG. 9). Bending can induce losses in the light that manages to go through the antireflective coating and starts propagating along the length of the fiber. Furthermore an additional absorbing coating (i.e. black paint) might be applied along the length of the optical fiber to help absorbing the light propagating through the fiber, to help removing the undesired back-reflections. Step (770) corresponds to FIG. 2B. As described above, the method depicted from FIGS. 2B-2H may be the followed to obtain the desired nanostructure on the optical fiber facet. The steps in FIGS. 2B-2H are summarized in FIG. 7 as photoresist development and etching (780) and metal coating (790).

In a further embodiment of the disclosure, the structure described above, in any of its different embodiments, could be used for a different detection technique, to detect molecules. Such technique comprises surface plasmonic resonance.

Plasmonic resonance, as those skilled in the art know, is a fundamental mechanism that can generate a field enhancement on the metallic nanoreliefs, which can be responsible for enhancing the Raman signal of the molecules. The electromagnetic field of the nanostructure field is enhanced at certain wavelengths (resonances) and when a molecule or other chemicals or media is close to the metallic nanostructure, the resonant wavelength changes. This shift in wavelength can be detected with appropriate electronic equipment, providing a way to detect molecules. Surface plasmonic resonance is not specific to a molecule, but rather it is a generic technique which can detect molecules without specificity. Specificity could be added by additional molecular recognition methods. For example, a functional layer may be added on top of the metallic layer, to provide binding sites to specific molecules. Alternatively, the metallic layer could be the functional layer as well (for example, gold, which is known to provide binding sites to specific molecules). Yet another alternative, as an example and not for limitation, would be to have a functional layer comprising two components, for example nanoparticles and a binding agent.

Figure 10:
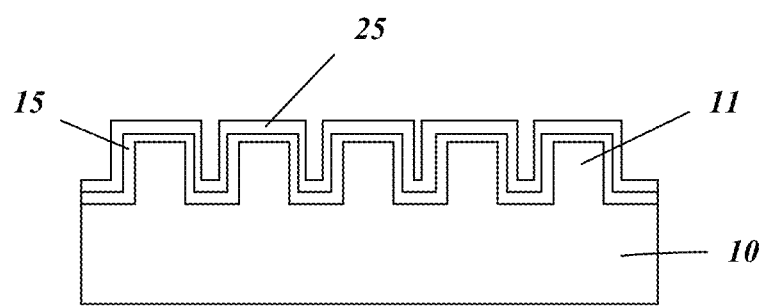
FIG. 10 depicts a metal coating on a nanopillars array on an optical fiber, with a functional layer on the metal coating.

FIG. 10 depicts an example embodiment of a surface plasmonic resonance detection nanostructure, where a functional layer (25) is added on top of a metallic layer (15), where the nanostructure (11) on an optical fiber substrate (10) are fabricated using one of the techniques and methods described herein above, in the present disclosure. The relative size and spacing of the nanostructure in FIG. 10 is not indicative of the real dimension and spacing.

For Surface Plasmon Resonance (SPR) detection a different measurement set-up would be needed, relative to Raman scattering, as it is understood by a person skilled in the art. For SPR a white light (encompassing wavelengths at least between 400 nm and 800 nm) may be used as a light source to illuminate the nanostructure through the optical fiber. A spectrometer may be used to detect the light diffracted from the nanostructure, or alternatively a monochromator may be used, by sweeping over the detection wavelengths to collect a signal at each wavelength in turn.

All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The examples set forth above are provided to give those of ordinary skill in the art a complete disclosure and description of how to make and use the embodiments of the surface enhanced Raman detection array nanostructure, and are not intended to limit the scope of what the inventors regard as their disclosure. Modifications of the above-described modes for carrying out the disclosure may be used by persons of skill in the separation and sensing of molecules, and are intended to be within the scope of the following claims.

A number of embodiments of the present disclosure have been described. Nevertheless, it will be understood that various modifications may be made without departing from the spirit and scope of the present disclosure. Accordingly, other embodiments are within the scope of the following claims.

The invention claimed is:

1. A method comprising:
providing an optical fiber having a planar facet end;
attaching a ferrule to the optical fiber adjacent to the planar facet end;
fitting the optical fiber with the ferrule on a spin coater;
coating the planar facet end of the optical fiber with the ferrule with a photoresist;
producing a pattern in the photoresist for a nanoscale structure by interference lithography;
developing the photoresist;
removing the photoresist and a portion of the optic fiber unprotected by the photoresist, thus obtaining a nanoscale structure in the optic fiber; and
depositing a layer of metal on the nanoscale structure.

2. The method of claim 1, wherein the nanoscale structure is a periodic surface-relief structure.

3. The method of claim 1, wherein the nanoscale structure is a non periodic surface-relief pattern.

4. The method of claim 1, wherein the nanoscale structure is a random surface-relief pattern.

5. The method of claims 2, wherein the relief pattern is configured to be antireflective.

6. The method of claim 1, wherein the nanoscale structure is an array of nanopillars on the planar facet end of the optical fiber, the array of nanopillars substantially perpendicular to the planar facet end.

7. The method of claim 6, wherein the nanopillars have a substantially cylindrical shape.

8. The method of claim 6, wherein the nanopillars have a substantially conical shape.

9. The method of claim 1, wherein a planar antireflective material is coated onto the facet of the optical fiber attached to the ferrule, prior to coating the photoresist, and the antireflective coating is removed during the step which removes the photoresist and a portion of the optic fiber.

10. The method of claim 1, wherein the removal process comprises ion milling or deep reactive ion etching or inductively coupled plasma etching or electron cyclotron resonance etching.

11. The method of claim 1, wherein the metal layer is deposited by e-beam or sputtering or thermal evaporation or chemical vapor deposition.

12. The method of claim 1, wherein the metal layer is selected from the group consisting of: silver, gold, aluminum, iridium, platinum, palladium and copper.

13. The method of claim 1, wherein the metal layer covers also the surface of the optic fiber between the nanopillars.

14. The method of claim 1, wherein the metal layer coverage is non-continuous.

* * * * *